United States Patent [19]

Milner

[11] Patent Number: 4,960,116

[45] Date of Patent: Oct. 2, 1990

[54] ORTHOPAEDIC SPLINTING MATERIAL

[75] Inventor: Richard Milner, Bishops Stortford, United Kingdom

[73] Assignee: Smith and Nephew Associated Companies p.l.c., United Kingdom

[21] Appl. No.: 204,084

[22] Filed: Jun. 8, 1988

[30] Foreign Application Priority Data

Jun. 12, 1987 [GB] United Kingdom ............... 8713746
Feb. 25, 1988 [GB] United Kingdom ............... 8804382

[51] Int. Cl.$^5$ .............................................. A61F 5/04
[52] U.S. Cl. .................................... 128/90; 128/91 R
[58] Field of Search ............ 128/155, 156, 165, 91 R, 128/90, 89 R; 524/199; 525/458; 428/266

[56] References Cited

U.S. PATENT DOCUMENTS

| | | | |
|---|---|---|---|
| 4,316,457 | 2/1982 | Liegeois | 128/90 |
| 4,427,002 | 1/1984 | Baron | 128/91 R |
| 4,427,003 | 1/1984 | Fennimore | 128/90 |
| 4,433,680 | 2/1984 | Yoon | 128/90 |
| 4,442,833 | 4/1984 | Dahlen | 128/90 |
| 4,502,479 | 3/1985 | Garwood | 128/90 |
| 4,570,622 | 2/1986 | von Bonin | 128/90 |
| 4,574,793 | 3/1986 | Lee | 128/90 |
| 4,638,795 | 1/1987 | Richter | 128/90 |
| 4,667,661 | 5/1987 | Scholz | 128/90 |
| 4,774,937 | 10/1988 | Scholz et al. | 128/90 |

FOREIGN PATENT DOCUMENTS 54-100181 8/1979 Japan.

Primary Examiner—Robert A. Hafer
Assistant Examiner—Michael Brown
Attorney, Agent, or Firm—Jacobs & Jacobs

[57] ABSTRACT

A low tack orthopedic splinting material which includes a substrate coated with a low tack water curable composition that has an isocyanate resin which has dissolved therein from 1 to 10% of a compound of the formula (VII): $R^1-X-(OCH_2CH_2)_n-O-CO-(NH-)_m-R^2$ wherein $R^1$ is alkyl of 1 to 14 carbon atoms, phenyl, phenyl substituted by alkyl of 1 to 12 carbon atoms or alkyl of 1 to 4 carbon atoms substituted by phenyl, $R^2$ is alkyl of 1 to 14 carbon atoms, phenyl, phenyl substituted by alkyl of 1 to 12 carbon atoms or alkyl of 1 to 4 carbon atoms substituted by phenyl, n is 6 to 100, m is 0 or 1 and x is a bond or $-(NH)_m-CO-$.

5 Claims, No Drawings

ORTHOPAEDIC SPLINTING MATERIAL

The present invention relates to an orthopaedic splinting material which comprises a substrate coated with a water curable composition containing an isocyanate resin and a surfactant.

Orthopaedic splinting materials which set on exposure to moisture to form a cast which immobilizes the required part of the body have been used for very many years. In the last few years substrates coated with isocyanate resins have been used with considerable success as orthopaedic splinting materials. Such materials have been described in U.S. Pat. Nos. 4667661, 4655208, 4433680, 4427003, 4309990, 4574793 and 4427002. Many commercially available isocyanate based splinting materials have suffered from the minor drawback that they are rather sticky during application. This problem was addressed in U.S. Pat. No. 4667661 where the solution employed was to incorporate a lubricant by chemically bonding it to the resin or by using an incompatible additive which forms a layer at the surface of the resin. The incompatible lubricants illustrated were polysiloxanes and surfactants or polymers comprised of hydrophilic groups which produced low tack products when coated onto the surface of the resin.

Unfortunately the provision of a layer of additives can itself lend to one or more problems such as an over slippy product, noticeable quantities of leachable materials being left in the setting water, high exotherm, poor pre-set lamination, rolls which unwind too easily, and the like None of these disadvantages is enough to prevent use of the products described in U.S. Pat. No. 4667661 but I believe it would be desirable to mitigate them. Furthermore I believe it would be desirable to have the option of avoiding having to chemically modify the resin or having to apply the additive to the surface after coating. I have now devised new surfactants that can be incorporated throughout the resin by the simple expedient of dissolving the surfactant into the resin prior to spreading the resin onto the substrate. The use of a compatible surfactant in this way allows for the preparation of a product which has a low tack after dipping in water, does not unroll too easily or too stiffy, does not leave excessive extractables in the dipping water and which forms a good quality cast or splint.

The present invention provides a compound of the formula (I)

$$R^1 \text{—}(OCH_2CH_2)_n\text{—}O\text{—}CO\text{—}(NH)_m\text{—}R^2 \qquad (I)$$

wherein $R^1$ is an alkyl group of 1 to 14 carbon atoms, a phenyl group, a phenyl group substituted by an alkyl group of 1 to 12 carbon atoms or an alkyl group of 1 to 4 carbon atoms substituted by a phenyl group; $R^2$ is an alkyl group of 1 to 14 carbon atoms, a phenyl group, a phenyl group substituted by an alkyl group of 1 to 12 carbon atoms or an alkyl group of 1 to 4 carbon atoms substituted by a phenyl group; n is 6 to 100; and m is 0 or 1

Most aptly $R^1$ is methyl, straight alkyl of 10 to 14 carbon atoms or alkylphenyl where the alkyl is of 1 to 12 carbon atoms. Favorably $R^1$ is nonylphenyl.

Most aptly $R^2$ is alkyl of 1 to 6 carbon atoms or phenyl. Preferably $R^2$ is phenyl.

Suitably n is 20 to 60, aptly 40 to 60. Preferably n is about 50. Preferably m is 1.

Particularly suitable compounds of formula (I) are those of formula (II)

$$4\text{—}(C_9H_{19})C_6H_4\text{—}(OCH_2CH_2)_n\text{—}OCONHC_6H_5 \qquad (II)$$

wherein n is as hereinbefore defined. The preferred compound of the formula (II) is that wherein n is 50.

The compounds of formula (I) may be prepared by the reaction of a compound of the formula (III) with (IV) or (V)

$$R^1\text{—}(OCH_2CH_2)_nOH \qquad (III)$$

$$R^2\text{—}NCO \qquad (IV)$$

$$R^3\text{—}CO\text{—}Cl \qquad (V)$$

wherein $R^1$, $R^2$ and n are as defined in relation to formula (I). The reaction may be performed under conventional conditions for the reaction of hydroxy compounds with acid chlorides or isocyanates.

The compounds of the formula (II) are most suitably prepared by the reaction of phenylisocyanate with a compound of the formula (VI)

$$4\text{—}(C_9H_{19})C_6H_4\text{—}(OCH_2CH_2)_n\text{—}OH \qquad (VI)$$

Wherein n is as hereinbefore defined.

Compounds of formulae (III) and (VI) can be made by condensing ethylene oxide onto the corresponding appropriate hydroxylic compound in conventional manner. Many such compounds are commercially available and some of the compounds of formula (IV) are well known surfactants.

The present invention provides a low tack orthopaedic splinting material which comprises a substrate coated with a water curable composition comprising an isocyanate resin which has dissolved therein from 1 to 10% by weight of a compound of the formula (VIII)

$$R^1\text{—}X\text{—}(OCH_2CH_2)_n\text{—}O\text{—}CO\text{—}(NH)_m\text{—}R^2 \qquad (VII)$$

wherein $R^1$, $R^2$, n and m are as defined in relation to formula (I) and X is a bond or a $\text{—}(NH)_m\text{—}CO\text{—}$ group.

Favorably X is a bond so that the compound of the formula (VII) is the same as that of formula (I).

When X is a $\text{—}(NH)_m\text{—}CO\text{—}$ group $R^1$ is most aptly the same as $R^2$. In such compounds $R^1$ and $R^2$ are preferably both phenyl. Such compounds may be prepared by reaction of a polyethylene glycol with a compound of the formulae (IV) or (V) as hereinbefore defined.

Most suitably the compound of the formula (VII) is present in the composition from 2 to 8% by weight.

When 1 to 10% by weight of a compound of the formula VII) is dissolved in an inherently tacky isocyanate resin, the resulting curable composition becomes one which is low tack on exposure to water so that the users gloves do not significantly stick to the resin. This invention provides a method of producing a low tack resin in such manner.

In a preferred aspect the present invention provides a low tack orthopaedic splinting material which comprises a substrate coated with a water curable composition comprising an isocyanate resin which has dissolved therein from 2 to 8% by weight of a compound of the formula (II)

$$4\text{—}(C_9H_{19})C_6H_4\text{—}(OCH_2CH_2)_n\text{—}OCONHC_6H_5 \qquad (II)$$

wherein n is a number from 20 to 60, is favorably 40 to 60 and is preferably 50.

Surprisingly, the use of the novel compatible surfactants allows low tack orthopaedic splinting bandages to be formed which laminate well, do not have high exotherm, do not give rise to large amounts of leachable materials and can unroll easily.

Prior art surfactants which are not chemically inert towards the resin or which tend to migrate to the surface of the resin are not suitable for use in this invention. The preferred surfactants (such as that of formula (I) wherein n is 50) are those which dissolve in to resin to form a homogeneous material.

The surfactant is most suitably employed in the resin at about 2 to 8% and preferably 3 to 7%, for example 4,5 or 6% (wt/wt).

The curable composition may be prepared by mixing the prepolymer and the surfactant of formula (I) in any convenient manner. The surfactant may be melted prior to mixing as this aids in the preparation of a homogeneous preparation. The surfactant readily dissolves in the resin which is much preferred. The curable compositions form part of this invention. The curable composition may contain a catalyst such as potassium carbonate, dimethylaminoethylether, or a dimorpholinodialkylether such as dimorpholinodiethylether or a tertiary aminoalkanol such as dimethylaminoethanol or (dimethylmorpholino)diethylether or the like. A preferred catalyst is (dimethylmorpholino) diethylether.

The composition may be spread on a substrate in a conventional manner, for example on leno gauze or a polyester or glass substrate or other substrates. Knitted substrates are presently preferred, especially those of glass.

Compounds of the formula (III) may be obtained commercially under such names as Dowfax (9N50) wherein n is 50. Such materials can sometimes contain a little water (for example 0.5%) so may be dried if desired before use or excess reagent employed to compensate for the water.

The compatibility of the resin and surfactant of formula (VII) can be observed by dissolving the surfactant into the warm resin in a glass bottle under dry conditions, sealing the bottle. If after a prolonged time, for example, several months, there is no observable tendency for the surfactant to separate from the resin, the surfactant is compatible with the resin. 2

The following examples illustrate the invention:

EXAMPLE 1

Preparation of Surfactant

Dowfax 9N50 (493.08 g) containing 0.096% water was placed under dry argon into a 700 ml resin flask and warmed until molten. Metatin 812ES (0.99 g) was added and thoroughly mixed in. To the stirred mixture, maintained at 65° C., was added phenylisocyanate (27.6 g) by syringe. The polymer was stirred for a further 3 hours at 70 ± 5° C. and then poured into a 500 g bottle and sealed.

EXAMPLE 2

Preparation of Resin containing Additive

A jar of surfactant of Example 1 was warmed in an oven at 100° C. until molten. A jar of resin was warmed in the same oven for 20 minutes. Under dry argon the surfactant (6.06 g) was weighted into resin (100 g) and stirred in. The bottle was sealed and placed on rollers until cold.

The resin was made from Isonate 143L (47.8%), Isonate 240 (14.7%), Voranol (3.5%), polypropylene glycol (31.9%), antifoam (0.3%), methane sulphonic acid (0.03%) bis (2,6-dimethylmorpholino-N-ethyl) ether (1.8%).

EXAMPLE 3

Preparation of Bandage

Resin containing additive was spread to 44% wt total wt onto a knitted glass substrate (10 cm × 100 cm) using a hopper and doctor knives in conventional manner under argon. The bandage was wound onto a core to form a roll and sealed into an aluminum foil pouch under argon.

EXAMPLE 4

Demonstration

A bandage was removed from a pouch (example 3) and immersed in a beaker of water. The bandage was squeezed three times under water to ensure wetting, removed, shaken and applied to a mandrel. The bandage was non-tacky, but did not unroll in an uncontrollable manner and was found to self-adhere very satisfactorily and to yield a good quality cast.

EXAMPLE 5-6

Examples 3 and 4 were repeated using 7 0 g of surfactant.

EXAMPLE 7-8

Examples 3 and 4 were repeated using 8 0 g of surfactant.

I claim:

1. A low tack orthopaedic splinting material which comprises a substrate coated with a water curable composition comprising an isocyanate resin which has dissolved therein from 1 to 10% by weight of a compound of the formula (VII):

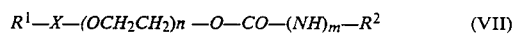
$$R^1-X-(OCH_2CH_2)_n-O-CO-(NH)_m-R^2 \qquad (VII)$$

wherein $R^1$ is alkyl of 1 to 14 carbon atoms, phenyl, phenyl substituted by alkyl of 1 to 12 carbon atoms or alkyl of 1 to 4 carbon atoms substituted by phenyl, $R^2$ is alkyl of 1 to 14 carbon atoms, phenyl, phenyl substituted by alkyl of 1 to 12 carbon atoms or alkyl of 1 to 4 carbon atoms substituted by phenyl, n is 6 to 100, m is 0 or 1 and X is a bond or $-(NH)_m-CO-$.

2. A splinting material according to claim 1 wherein X is a bond.

3. A splinting material according to claim 2 wherein m is 0 and the compound of formula (VII) is present in an amount of from 2 to 8% by weight.

4. A splinting material according to claim 2 wherein the compound of formula (VII) is of formula (II)

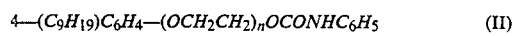
$$4-(C_9H_{19})C_6H_4-(OCH_2CH_2)_nOCONHC_6H_5 \qquad (II)$$

wherein n is 40 to 60.

5. A sprinting material according to claim 4 wherein n is about 50.

* * * * *